United States Patent
Villain et al.

(10) Patent No.: US 10,669,307 B2
(45) Date of Patent: Jun. 2, 2020

(54) DEVICE, USE OF SAID DEVICE, AND METHOD FOR SEPARATING SUBSTANCES WITH AN IMPROVED UTILIZATION OF THE CAPACITY OF CHROMATOGRAPHIC MEDIA

(71) Applicant: Sartorius Stedim Biotech GmbH, Göttingen (DE)

(72) Inventors: Louis Villain, Hannover (DE); Jörg Mittelstät, Göttingen (DE); Ana Raquel Santos De Matos Fortuna, Magdeburg (DE); Katrin Töppner, Osterode (DE)

(73) Assignee: Sartorius Stedim Biotech GmbH, Göttingen (DE)

( * ) Notice: Subject to any disclaimer, the term of this patent is extended or adjusted under 35 U.S.C. 154(b) by 201 days.

(21) Appl. No.: 15/323,778

(22) PCT Filed: May 12, 2015

(86) PCT No.: PCT/EP2015/000978
§ 371 (c)(1),
(2) Date: Jan. 4, 2017

(87) PCT Pub. No.: WO2016/005016
PCT Pub. Date: Jan. 14, 2016

(65) Prior Publication Data
US 2017/0166606 A1  Jun. 15, 2017

(30) Foreign Application Priority Data
Jul. 10, 2014  (DE) .......................... 10 2014 010 353

(51) Int. Cl.
*B01D 15/38* (2006.01)
*B01D 15/18* (2006.01)
(Continued)

(52) U.S. Cl.
CPC ............ *C07K 1/22* (2013.01); *B01D 15/1871* (2013.01); *B01D 15/363* (2013.01);
(Continued)

(58) Field of Classification Search
CPC .............. B01D 15/1871; B01D 15/363; B01D 15/3809; B01D 15/38; B01D 15/18;
(Continued)

(56) References Cited

U.S. PATENT DOCUMENTS

| 5,071,547 A | 12/1991 | Cazer et al. |
| 7,901,581 B2 | 3/2011 | Bryntesson et al. |
| 2011/0272357 A1* | 11/2011 | Gorak ...................... C07K 1/20 210/656 |

FOREIGN PATENT DOCUMENTS

| DE | 690 19 243 | 11/1995 |
| DE | 198 12 821 | 9/2006 |

(Continued)

OTHER PUBLICATIONS

Deans et al., "Use of heart cutting in gas chromatography: A review", Journal of Chromatography, vol. 203, Jan. 9, 1981, pp. 19-28.

*Primary Examiner* — Robert Clemente
*Assistant Examiner* — Akash K Varma
(74) *Attorney, Agent, or Firm* — McDonnell Boehnen Hulbert & Berghoff LLP (57) ABSTRACT

The present invention relates to a device for separating and/or isolating substances in or from a mixture with improved utilization of the capacity of chromatographic media, the device comprising a first chromatography system, a second chromatography matrix downstream of the first chromatography system, and a sensor for detecting the substances present in the fluid. Furthermore, the present invention relates to both the use of said device and a method (Continued)

for separating and/or isolating substances in or from a mixture in a fluid.

17 Claims, 3 Drawing Sheets

(51) Int. Cl.
| | |
|---|---|
| B01D 15/36 | (2006.01) |
| C07K 1/22 | (2006.01) |
| C07K 1/18 | (2006.01) |
| C07K 14/765 | (2006.01) |
| G01N 30/46 | (2006.01) |
| G01N 30/88 | (2006.01) |
| C07K 1/16 | (2006.01) |
| C07K 1/20 | (2006.01) |

(52) U.S. Cl.
CPC ............ B01D 15/3809 (2013.01); C07K 1/16 (2013.01); C07K 1/18 (2013.01); C07K 1/20 (2013.01); C07K 14/765 (2013.01); G01N 30/461 (2013.01); G01N 30/88 (2013.01); G01N 2030/8831 (2013.01)

(58) Field of Classification Search
CPC . B01D 15/36; C07K 1/22; C07K 1/16; C07K 1/18; C07K 1/20; C07K 14/765; G01N 30/88; G01N 30/461; G01N 30/46; G01N 2030/8831
USPC .......................................................... 210/85
See application file for complete search history.

(56) References Cited

FOREIGN PATENT DOCUMENTS

| | | | |
|---|---|---|---|
| EP | 1 718 668 | 11/2006 | |
| WO | WO 99/34220 | 7/1999 | |
| WO | WO 2003/051483 | 6/2003 | |
| WO | WO 2010/151214 | 12/2010 | |
| WO | WO 2012/057676 | 5/2012 | |
| WO | WO-2012057676 A1 * | 5/2012 | ......... B01D 15/1871 |

* cited by examiner

DEVICE, USE OF SAID DEVICE, AND METHOD FOR SEPARATING SUBSTANCES WITH AN IMPROVED UTILIZATION OF THE CAPACITY OF CHROMATOGRAPHIC MEDIA

CROSS-REFERENCE TO RELATED APPLICATIONS

The present application is a section 371 U.S. national phase of PCT/EP2015/000978, file May 12, 2015, which claims priority to German Patent Application No. 10 2014 010 353.6, filed Jul. 10, 2014, the contents of which are hereby incorporated by reference.

FIELD OF THE INVENTION

The present invention relates to a device for separating and/or isolating substances in or from a mixture with improved utilization of the capacity of chromatographic media, the device comprising a first chromatography system, a second chromatography matrix downstream of the first chromatography system, and a sensor for detecting the substances present in the fluid. Furthermore, the present invention relates to both the use of said device and a method for separating and/or isolating substances in or from a mixture. More particularly, the present invention relates to a device for removing at least one contaminant from at least one target substance in a liquid medium (fluid), the liquid medium containing the at least one contaminant and the at least one target substance being guided through the device according to the invention.

BACKGROUND OF THE INVENTION

The production of a recombinant biotechnological or biopharmaceutical product (protein, virus, RNA, DNA, antibody, coagulation factor, enzyme) involves not only the expression of the target substance in cell cultures in fermenters, which is also referred to as upstream processing (USP), but also the purification of the target substance from contaminants found together in solution (host cell proteins, DNA, RNA, media constituents, undesired viruses, etc.). The latter step is also referred to as downstream processing (DSP). The central step in DSP is the chromatographic separation of the substances situated in the inflow, the feedstream. This involves the binding of certain substances to a solid matrix, which can be a membrane, a particulate gel or a monolith. Fundamentally, chromatographic steps in DSP are carried out in two configurations. Depending on whether the target substance or the target molecule binds to the chromatographic matrix and is then eluted, or resides in the mobile phase and undesired contaminants bind to the matrix, said configurations are referred to as bind-and-elute or as flow-through applications.

The binding capacity of chromatographic matrices both for target molecules or contaminants is limited and the costs can be very high, for example for antibody purification using affinity matrices. Consequently, from the perspective of process economy, a favorable situation ensues when chromatographic matrices are dimensioned as small as possible and the available binding capacity is utilized as fully as possible. This is limited by the fact that there should be avoidance of a loss due to overloading of a column in bind-and-elute mode or of an input of contamination due to an overloading of the chromatographic matrix in flow-through mode. The loading status of a chromatographic matrix can be monitored by means of a sensor, such as, for example, a UV or IR sensor, which is situated at the output side. If the capacity of a matrix is exceeded, this results in a change in the signal intensity at the output of the medium. The attainment of a predefined value can be used as a termination criterion, at which the loading of the column is stopped. An important parameter in this method is the signal-to-noise ratio of customary detectors used in processes, and this can have a direct effect on the losses of target molecule (bind and elute) or on the contamination of the feedstream with secondary components (flow-through).

Therefore and owing to (i) batch-dependent variations in the binding capacity of the chromatographic media, (ii) errors in the case of scaled enlargement of established processes, and (iii) the need to take possible extreme cases into account, for example for variations in the concentration of the molecule in the feedstream, but also in pH and in conductivity, the theoretically available capacity of a chromatographic matrix is in practice not fully utilized in order to be safe. Generally, the utilization of the capacity of the chromatographic matrix is estimated to be only approx. 60%. Although the loss of target molecule or the contamination of the process stream can be avoided in this way, the overdimensioning of the chromatographic matrix leads to an economically unfavorable situation. An optimization of the utilization of the capacity of the chromatographic matrix can therefore provide a large savings potential in process time and in material costs, especially in the case of cost-intensive chromatographic materials such as protein A.

WO 2010/083859 A1 discloses a device and a method for isolating substances from a mixture, the device comprising at least one diffusively operable and one convectively operable chromatography matrix. In the examples mentioned, the connection of the diffusively operable matrix (column) to a smaller convectively operable matrix (membrane adsorber) leads to an improved, i.e., steeper, breakthrough behavior during loading and a twice as high productivity (mg/ml× min). Owing to the combination of a column with a membrane adsorber, it is possible to increase the efficiency of the separation process and to improve the breakthrough behavior of the separation process.

WO 2010/151214 A1 discloses a system which captures the loading status of a chromatographic column, by capturing the input signal of a column via a first detector and also the output signal via a second detector. The ratio of the input signal and the output signal yields conclusions with regard to the loading status of the column. This information can be used in the context of a multistep chromatographic process in order to define the start and stop of different process steps, such as loading for example. The device disclosed in WO 2010/151214 A1 makes it possible to determine binding capacities of chromatographic columns and fundamentally makes use of two sensors in order to ascertain the loading status of a column.

WO 99/34220 A2 discloses a method which can capture via an online detection method the loading status of a chromatographic unit containing a solution consisting of a target molecule and contaminants. In said method, a small portion of the eluate of the chromatographic unit is deflected from the eluate stream into a separate detection unit. The separate detection unit, which can, for example, be a chromatographic structure, ascertains the proportion of contaminants and unbound target molecule in less than 20% of the total elution time. Loading can be terminated when a defined concentration of target molecule in the eluate is exceeded. In this method, it is necessary to divert a portion of the eluate of a chromatographic column into a separate detection unit.

A return of the proportion of the eluate which was used for the analysis back into the eluate stream is not envisaged or is made impossible by the chromatographic steps during the analysis and the solvents used.

U.S. Pat. No. 7,901,581 B2 discloses a system composed of at least three chromatography matrices which are connected to one another by valves and can be continuously operated as a "simulated moving bed" concept. The system is controlled by means of a control unit and refers to UV measurement values of the eluates of the individual units. One function of the structure is the catching of unbound target molecule from the loading solution or wash fraction of a first column by a downstream column, with at least three separately controllable chromatographic matrices being required. It is therefore possible to prevent unbound target molecule from being lost from the process.

EP 1 718 668 B1 discloses a method for purifying antibodies from a solution containing contaminants. In said method, said solution is contacted with a chromatographic matrix on which multimodal ligands have been immobilized. In this connection, the multimodal ligands comprise at least one cation-exchanging group and one aromatic or heteroaromatic ring system. The chromatographic matrix can be particulate, a monolith or a membrane. In this connection, the antibody-containing solution used for loading the matrix is an eluate from an affinity-chromatographic step such as protein A affinity chromatography. Mentioned as possible operating modes of the multimodal chromatography matrix are both the flow-through application, in which only contaminants and, inter alia, also protein A adsorb, and the bind-and-elute application, in which the antibodies and the contaminants adsorb and can then be eluted separately. A switch between the two operating modes can be made by adjusting the pH of the solution after the affinity-chromatographic step. The disclosure mentioned here describes the use of a multimodal chromatography matrix alone or in a two-column arrangement following an affinity-chromatographic step with the goal of a maximally economical purification of antibodies. In the case of the two-column arrangement, the advantages of the combination of two different matrices (affinity chromatography and multimodal cation-exchange chromatography) and thus of two different adsorption modes are paramount. These allow, for example, the binding of washed-out protein A or contaminants which coelute with the antibody from protein A on the multimodal matrix, whereas the antibody remains in the mobile phase or can be eluted separately from the contaminants. Strictly speaking, the loading capacity of the protein A column cannot be utilized more efficiently in this method, since (i) a sensor for detecting the breakthrough following the affinity-chromatographic step is missing, (ii) the flow-through during loading of the affinity-chromatographic column is not guided onto the multimodal matrix and (iii) the eluate of the affinity-chromatographic step is loaded onto the multimodal matrix. Therefore, savings in the capacity of the affinity-chromatographic matrix are barely possible with this method.

When loading a chromatographic column with the feed-stream containing a target molecule, the loading operation is frequently prematurely terminated in order to avoid an overloading of the column and thus a loss of target molecule. The available capacity of the column is therefore not fully utilized. Especially in the case of expensive column materials, such as protein A for example, the result is an economically disadvantageous situation. Furthermore, the number of DSP cycles per batch or throughput is generally defined by the size of the available column material. Therefore, a longer total duration and a reduced efficiency of the process can arise as a further consequence.

SUMMARY OF THE INVENTION

It is therefore an object of the present invention to provide a device which overcomes the abovementioned disadvantages and leads to an improved utilization of the capacity of chromatographic media.

This object is achieved by the embodiments characterized in the claims.

More particularly, what is provided is a device for separating and/or isolating substances in or from a mixture in a fluid, comprising a first chromatography system which comprises one or more chromatography matrices, a sensor downstream of the first chromatography system for detecting the substances present in the fluid, and a second chromatography matrix downstream of the sensor, the second chromatography matrix being connected downstream of the first chromatography system such that the fluid leaving the chromatography system is guidable through the second chromatography matrix. The chromatography matrices of a chromatography system can be connected to one another in parallel or in series therein.

It has been found that, surprisingly, the capacity of a chromatography medium by downstream connection of a sensor for detecting the substances present in the fluid and of a preferably smaller chromatographic matrix having only a small proportion of the capacity of the first chromatography system, which can for example also be referred to as main column, the capacity of the main column can be utilized distinctly more efficiently during loading without occurrence of a loss of product.

The device according to the invention comprises a sensor which is connected upstream of a second chromatographic matrix, which, for its part, is in turn connected downstream of a first chromatographic system. The present invention therefore differs from WO 2010/151214 A1 in that, with the aid of only a single sensor, the loading status of the first chromatographic system (main column), i.e., the breakthrough of the target molecule or of the contaminant and thus the overloading of the column, can be determined on the basis of a change in the slope of the breakthrough signal. According to the invention, it is consequently possible to dispense with a further sensor which captures the input signal of a column via an upstream detector. In said invention, with sufficient dimensioning of the second chromatographic matrix connected downstream of the sensor, an early detection of the breakthrough of the target molecule in the case of a bind-and-elute mode or of the contaminant in the case of a flow-through mode is possible without material needing to be deflected into a separate analysis unit, as is absolutely required in WO 99/34220 A2. Furthermore, the device according to the invention is, unlike U.S. Pat. No. 7,901,581 B2, suitable for batch processing and can, unlike EP 1 718 668 B1, lead to a saving of expensive chromatographic matrices, such as protein A for example.

According to the present invention, the expression "separating and/or isolating", as used herein, is not subject to any specific restriction and relates to any operation suitable for removing a substance from a mixture. Here, the expression "separating and/or isolating" means, for example, that a desired target substance is isolated, in the sense of a purification, from a mixture present in a fluid, or that an impurity is removed in order to clear the mixture of said impurity. Said expression also contains no restriction whatsoever with regard to the quantities to be separated and relates to both the separation of analytical quantities of substance and the preparative purification of larger quantities of substance, which may arise in a production process for example.

Furthermore, the expression "mixture" relates to any mixture containing more than one substance. According to the present invention, such a mixture can contain one component in great excess, with the remaining components of the mixture being present in small or the smallest quantities. However, the term "mixture" also encompasses those mixtures containing multiple components present in medium concentration.

The device according to the invention is distinguished by the specific arrangement of the first chromatography system and of the second chromatography matrix and also of the interposed sensor. The first chromatography system and/or the second chromatography matrix are not subject to any particular restriction and can be designed for both a bind-and-elute, mode and a flow-through mode, preference being given to a bind-and-elute mode. However, the first chromatography system and the second chromatography matrix are preferably such materials involving the same separation mode. This means that, when the first chromatography system is, for example, designed as bind-and-elute mode in the form of a main (separation) column, the downstream second chromatography matrix, which can generally also be referred to as trap column or capture column, should be likewise operated in said mode. In another embodiment according to the invention, the first chromatography system and the second chromatography matrix operate according to different separation modes.

According to the invention, it is, for example, possible to use a combination of a diffusively operable and a smaller convectively operable chromatography matrix, i.e., separation column and membrane adsorber, as described in WO 2010/083859 A1, to which full reference is made here. More particularly, preference is given to using, as separation column, diffusively operable chromatography matrices comprising regularly or irregularly shaped beads having preferably ion-exchanging groups (corresponding to the first chromatography system). Particularly preferably, the first chromatography system comprises a gel chromatography matrix. According to a further preferred embodiment of the present invention, the first chromatography system comprises a membrane adsorber or monolith. In this case, convectively operable media are all media in which mass transfer is mainly determined via convective processes and not via diffusive processes.

The second chromatography matrix of the device according to the invention is preferably a planar structure. In this case, the expression "planar" is understood to mean a structure in which the extent in the x-axis and y-axis in the Cartesian, three-dimensional coordinate system exceeds the extent in the z-axis many times over. Said planar structure can, for its part, be used in the form of flat modules, stacked modules, spiral-wound modules or cylinders. Among the planar carrier materials, particular preference is given to filters, membranes, nonwovens, wovens or combinations thereof. Such a chromatography matrix can also be used as a component of the first chromatography system.

"Carrier materials" are to be understood to mean materials having, bonded on the surface thereof, functional groups which make it possible to bind substances from liquid fluids or gaseous fluids. However, the carrier materials as such are generally not adsorptive.

In a further preferred embodiment, the second chromatography matrix is monolithic, i.e., it is not built up from a multiplicity of beads, but is instead a one-piece, cohesive and porous monolith. Commercially available, monolithic matrices are sold by the companies BIA, Ljubljana, Slovenia (CIM disks) and Biorad, Hercules, Calif., USA (UNO monolith). Such a chromatography matrix can also be used as a component of the first chromatography system.

A further embodiment of the present invention relates to a device as defined above, with the second chromatography matrix being a membrane adsorber having at least one membrane. According to the invention, it is most preferably possible to use, as second chromatography matrices, membrane adsorbers comprising at least one microporous membrane optionally bearing on its inner and outer surfaces functional groups which enter into a physical and/or chemical interaction with the substances.

"Chemical interaction" is to be understood hereinafter to mean any covalent, ionogenic and/or electrostatic-interaction-based or hydrophobic-interaction-based (e.g., Van der Waals interaction) binding interaction between the functional groups and the adsorbates.

Furthermore, porous, particulate adsorbents comprising regularly or irregularly shaped beads preferably having ion-exchanging groups, more particularly gel chromatography matrices, are preferably used as second chromatography matrix. Such chromatography matrices can also be used as a component of the first chromatography system.

According to the present invention, the expression "downstream" merely means that the second chromatography matrix is arranged, in the direction of flow, after the sensor, which is in turn arranged, in the direction of flow, after the first chromatography system, and is furthermore not to be understood as restrictive. This applies, mutatis mutandis, to the expression "upstream". Preferably, the fluid leaving the first chromatography system is completely guidable through the second chromatography matrix, meaning that the entire fluid which exits from the first chromatography system and is analyzed by means of an interposed sensor can be directly and completely guided through the second chromatography matrix.

According to a particularly preferred embodiment of the present invention, the combination of chromatography system, chromatography matrix and the sensor is present in a compact or unified assembly, making it possible to carry out simple handling without any problems, for example for maintenance or for replacement of the device.

The term "chromatography matrix" used according to the invention encompasses any material, on the surface of which it is possible to bind at least one component of a fluid in contact with the material. The capability for adsorption in the context of the present invention can be inherent to the material of the "chromatography matrix", such as, for example, in the case of activated carbon or hydroxylapatite; however, it can also be achieved by modification of a carrier material with one or more ligands, with the first chromatography system and/or the second chromatography matrix comprising at least one ligand which interacts via at least one chemical and/or physical interaction with at least one substance in the mixture. A chromatography matrix can be a component of the first chromatography system and of the second chromatography matrix.

Examples of such usable ligands are ligands which interact with adsorbates via at least one chemical and/or physical interaction, more particularly ion exchangers, salt-tolerant ligands, chelating agents, thiophilic or hydrophobic ligands of various chain lengths and configurations, "reversed-phase" ligands, reactive dyes and other dyes, inorganic molecules and ions and also organic and inorganic compounds thereof, affinity ligands, including low-molecularweight uncharged or charged organic molecules, amino acids and analogs thereof, coenzymes, cofactors and analogs thereof, substrates and analogs thereof, endocrine and exocrine substances such as hormones and effectors acting like hormones and also analogs thereof, enzyme substrates, enzyme inhibitors and analogs thereof, fatty acids, fatty acid derivatives, conjugated fatty acids and analogs thereof, nucleic acids such as DNA and analogs and derivatives thereof, RNA and analogs and derivatives thereof, monomers and analogs and derivatives thereof, oligomers to polymers and analogs and derivatives thereof, high-molecular-weight carbohydrates, linear or branched, unsubstituted or substituted, glycoconjugates, such as heparin, amylose, cellulose, chitin, chitosan, monomers and oligomers and also derivatives and analogs thereof and also lignin and derivatives and analogs thereof.

Further examples are high-molecular-weight ligands such as proteins and their oligomers, multimers, subunits and also parts thereof, peptides, polypeptides, analogs and derivatives thereof, lectins, antibodies and parts thereof, fusion proteins, haptens, enzymes and subunits and also parts thereof, structural proteins, receptors and effectors and also parts thereof, viruses and parts thereof, xenobiotics, pharmaceuticals and active pharmaceutical ingredients, alkaloids, antibiotics, biomimetics and catalysts.

According to a preferred embodiment of the present invention, at least the first chromatography system and/or the second chromatography matrix comprises one or more ligands which interact with adsorbates via at least one chemical and/or physical interaction and which are selected from the group comprising ion exchangers, salt-tolerant ligands, chelating agents, thiophilic or hydrophobic ligands of various chain lengths and configurations, "reversed-phase" ligands, reactive dyes and other dyes, inorganic molecules and ions, organic and inorganic compounds thereof, affinity ligands, high-molecular-weight ligands, enzymes and subunits and also parts thereof, structural proteins, receptors and effectors and also parts thereof, viruses and parts thereof, xenobiotics, pharmaceuticals and active pharmaceutical ingredients, alkaloids, antibiotics, biomimetics and catalysts.

The ligands of the first chromatography system and of the second chromatography matrix can be identical or different from one another and interact with adsorbates by means of identical and/or different chemical and/or physical interactions.

Particularly preferred ligands bonded to the first chromatography system and/or the second chromatography matrix are trimethylamine, N,N-diethyl-N-(2-hydroxy-1-propyl) ammonium methyl, diethylaminoethyl, 2,2'-iminodiethanol, carboxymethyl, sulfopropyl and sulfomethyl ligands. As described above, the first chromatography system and the second chromatography matrix preferably each have at least one ligand which interacts with the substances in the mixture via the same type of binding interaction. Particularly preferably, the first chromatography system and the second chromatography matrix have at least one identical ligand. Said ligands can interact with the adsorbates via identical or different chemical or physical interactions. More particularly preferably, the first chromatography system and the second chromatography matrix each have different ligands. Said ligands can interact with the adsorbates via identical and/or different chemical and/or physical interactions.

According to the invention, the second chromatography matrix can have a capacity which is identical in comparison with the first chromatography system or a capacity which is smaller. Preferably, the second chromatography matrix has a capacity which is distinctly smaller in comparison with the first chromatography system, the term "capacity which is distinctly smaller" being understood to mean less than 50% of the binding capacity of the upstream first chromatography system. Preferably, the capacity of the second chromatography matrix is less than 30%, more preferably less than 20% and particularly preferably less than 10%, of the binding capacity of the upstream first chromatography system. On the other hand, the capacity of the second chromatography matrix is preferably at least 0.005%, more preferably at least 0.01% and particularly preferably at least 0.1%, of the binding capacity of the upstream first chromatography system, the lower limit being greatly dependent on the detection sensitivity of the downstream detector, and so said second matrix can, as trap column or capture column, catch the target substances or contamination which have undergone breakthrough.

The term "binding capacity" describes the quantity of a target molecule which can be bound per unit volume of the chromatographic medium (unit g/l), and is referred to as static or dynamic binding capacity depending on the method used for determination. The dynamic binding capacity of a chromatographic medium is the quantity of target molecule which the medium will bind under certain flow conditions before a significant proportion, for example 10% of the concentration of the molecule in the feed medium, breaks through. The static binding capacity of a chromatographic medium is the total quantity of target molecule which the medium will bind and can be determined independently of the flow rate, for example in a batch test. The static binding capacity is therefore always greater than the dynamic binding capacity of a chromatographic medium.

The sensor which is arranged between the first chromatography system and the second chromatography matrix in the device according to the invention is not particularly restricted, so long as said sensor is suitable for the detection of the substances present in the fluid. Suitable sensors are well known to a person skilled in the art, it being possible to mention, for example, absorption spectroscopy as the detection principle for the sensor. Besides absorption spectroscopy (more particularly UV, IR and terahertz spectroscopy), the use of refractometry, conductometry, radiometry, fluorescence spectroscopy especially of surface fluorescence quenching, ATR (attenuated total reflection) infrared spectroscopy especially of surface plasmon resonance spectroscopy (SPRS), of manometry, potentiometry, polarimetry, impedance spectroscopy, NMR spectroscopy, Raman spectroscopy, turbidimetry, nephelometry, of ultrasound transit time and the combination of multiple techniques is, for example, also possible as detection principle for the sensor. Preferably, the device according to the invention comprises a UV, IR, pH, pressure or conductivity sensor.

The device according to the invention comprises a sensor which is connected upstream of the second chromatographic matrix, which, for its part, is in turn connected downstream of the first chromatographic system. According to the invention, the sensor is preferably nondestructive with regard to the target molecule. Preferably, the device according to the invention consists of these components. Particular preference is given to a device in which a UV, IR, pH, pressure or conductivity sensor is arranged between a first chromatography system, containing or consisting of a gel chromatography matrix, as main separation column and a downstream membrane adsorber as second chromatography matrix. However, according to a further embodiment of the present invention, the device can comprise one or more additional membrane adsorbers which are connected upstream of the sensor. This makes it possible to further increase the sensitivity of detection for breakthroughs of the target molecule and the loss of product can be further minimized.

A further aspect of the present invention relates to a method for separating and/or isolating substances in or from a mixture in a fluid, comprising the steps of guiding the fluid through the above-defined device according to the invention and collecting the fluid which has been guided through.

According to the present invention, the flow rate at which the fluid is guided through the above-defined device is within a range from 0.01 ml/min to 1000 ml/min, preferably within a range from 1 ml/min to 200 ml/min, particularly preferably within a range from 2 ml/min to 100 ml/min and most preferably within the range from 2.5 ml/min to 50 ml/min.

According to the present invention, the particular starting concentration(s) of the target substance(s) in the fluid that is/are to be separated or to be isolated is/are within a range from 0.001 mg/ml to 1000 mg/ml, preferably within a range from 0.01 mg/ml to 50 mg/ml, particularly preferably within a range from 0.1 mg/ml to 20 mg/ml and most preferably within a range from 1 mg/ml to 10 mg/ml, based on the individual substance.

A further embodiment relates to a method as defined above, wherein the mixture is a solution composed of a synthesis reaction, a biomolecule-containing fluid or a bioparticle-containing fluid. "Biomolecule-containing fluid" is to be understood here to mean a fluid containing substances selected from the group of the amino acids and analogs thereof, coenzymes, cofactors and analogs thereof, of the endocrines and of the exocrine substances, such as hormones and effectors acting like hormones, and analogs thereof, enzymes and subunits and also parts thereof, enzyme substrates, enzyme inhibitors and analogs thereof, fatty acids, fatty acid derivatives, conjugated fatty acids and analogs thereof, of the deoxyribonucleic acids and ribonucleic acids and analogs and derivatives thereof, single- to multistranded plasmids, cosmids and other constructs, carbohydrates and glycoconjugates, proteins and their oligomers, multimers, subunits and also parts thereof, peptides, polypeptides, analogs and derivatives thereof, lectins, antibodies and parts thereof, fusion proteins, haptens, structural proteins, receptors and effectors and also parts thereof, xenobiotics, pharmaceuticals, alkaloids, antibiotics, biomimetics, allergens or combinations thereof.

"Bioparticle-containing fluid" is to be understood here to mean a fluid containing particles selected from the group of the viruses and parts thereof, prions and parts thereof, microorganisms, prokaryotes, protozoa, yeasts, fungi, eukaryotes of animal and plant origin, cell wall constituents from prokaryotes, protozoa, yeasts, fungi, eukaryotes of animal and plant origin and parts thereof, biological membranes and parts thereof, subcellular, biological membranes and parts thereof or combinations thereof.

Preferably, substances are obtained by means of the method according to the invention, wherein the mixture is a solution of a synthetically or biologically produced product, or a natural substance. Furthermore, the mixture is preferably a protein-containing solution or an antibody-containing solution.

A further aspect of the present invention relates to the use of the device according to the invention for separating and/or isolating at least one target substance in or from a mixture in a fluid. Such a use is not restricted to a particular technical area and encompasses all applications in which substances need to be separated or isolated from a mixture. Examples of such areas are chemical, pharmaceutical, medical or biological research or production.

According to the invention, the use of the device according to the invention makes it possible to better utilize the capacity of the first chromatography system. Preferably, the present invention allows an over 60%, particularly preferably over 70%, utilization of the capacity of the first chromatography system.

The present invention will be described in more detail below by means of examples and with reference to the attached figures, but without being restricted in any way thereby. In particular, it should be pointed out that the UV signal was measured both after the first chromatography system and after the second chromatography matrix, the measurement after the second chromatography matrix not necessarily belonging to the concept presented here and serving only for illustration. The figures show:

DESCRIPTION OF THE INVENTION

Examples

Materials and Methods

All the experiments were carried out on the FPLC system ÄktaPrime plus from GE Healthcare. UV absorption was measured at 280 nm and chromatograms were evaluated with the aid of the software PrimeView 5.31 (GE Healthcare). Dead volumes were determined by the injection of a nonbinding, UV-active tracer molecule (20% acetone), which was added to the particular equilibration buffer. Samples up to a volume of 150 ml were injected with the aid of a Superloop (GE Healthcare). In the case of loading volumes above a volume of 150 ml, the samples were applied via one of the buffer valves of the ÄktaPrime. The flow rate for equilibration, loading, washing and elution was 5 ml/min for the experiments with the HiTrap Protein A HP column, and 10 ml/min for experiments with Sartobind® Q Nano capsules. All the buffer substances were from Carl Roth (Karlsruhe) or Merck (Darmstadt). Adjustment of the pH of the solutions was done at room temperature.

Protein A Chromatography

For the experiments with protein A chromatography, the following buffers were used:
A) 1×PBS pH 7.4 ($Na_2HPO_4$ (10 mM), $KH_2PO_4$ (1.8 mM), NaCl (137 mM), KCl (2.7 mM), 15 mS/cm, and
B) 0.1 M glycine/HCl, pH=3.5, 4 mS/cm for elution Different concentrations (0.5-5 mg/ml) of human IgG (SeraCare, HS-475) and 1 mg/ml BSA in buffer A (see above), or a prefiltered undiluted cell-free culture supernatant of an $IgG_1$-expressing CHO (Chinese Hamster Ovary) cell line (DG44 Cellca), were used for loading. The detailed description of the experimental procedures is found in the respective exemplary embodiments.

Anion-Exchange Chromatography

For the experiments with anion-exchange chromatography, the following buffers were used:
C) Tris-HCl pH 7.4 (20 mM) 1.8 mS/cm, and
D) Tris-HCl pH 7.4 (20 mM), NaCl (1 M), 87 mS/cm for elution The loading solution was prepared by dissolving bovine serum albumin (BSA) (2 g/l, Kraeber & Co No. 4909 2052) and lysozyme (5 g/l, Roth No. 8259.2) in buffer C and filtering this solution across a Sartolab® filter (PESU membrane, 0.2 μm pore size, Sartorius Stedim Biotech GmbH). The influence of the membrane adsorber (see examples below) was investigated by flushing the unit (Sartobind® Q Nano with and without downstream membrane adsorber) with 30 ml of buffer C, then loading with 120 ml of BSA (2 mg/ml), lysozyme (5 mg/ml) in buffer C, washing with 30 ml of buffer C, then eluting with 30 ml of buffer D and lastly equilibrating again with 30 ml of buffer C.

Determination of the Degree of Breakthrough and of Loss of Product

In all the described experiments, the column material has only a low capacity for contaminants and a distinctly higher capacity for the target molecule; accordingly, the breakthrough of the contaminants occurs first and is visible as a plateau in the UV absorption at the output of the column. Only at higher loading volume is the capacity for the target molecule exhausted and the breakthrough of the target molecule observed. The degree of the breakthrough of the target molecule can be calculated on the basis of the following relationship:

$$\text{Breakthrough of target molecule (\%)} = \frac{(UV_X - UV_{Contaminant})}{(UV_{Total} - UV_{Contaminant})} \times 100$$

where $UV_x$ is the UV signal at a particular loading volume [mAU], $UV_{contaminant}$ is the UV signal at complete breakthrough of the contaminant (base line) [mAU] and $UV_{Total}$ is the UV signal at complete breakthrough of the contaminant and of the target molecule [mAU].

Relative loss of product can be directly calculated from the breakthrough curve via the ratio of the area integral of the UV absorption of loaded target molecule and unbound target molecule (below the breakthrough curve):

$$\text{Loss of product (\%)} = \frac{\text{Area below the curve}}{\text{Total area}} \times 100$$

Example 1-Influence of the Bed Height of the Downstream Membrane Adsorber

In the first example, IgG (SeraCare, HS-475) is purified with the aid of protein A affinity chromatography. Protein A binds with very high affinity to the Fc region of the heavy chain of immunoglobulins, with contaminants binding only very weakly to the column material and being in the flow-through during loading of the column. The main medium used (corresponding to the first chromatography system) is a protein A column (HiTrap Protein A, article No. 17-0403-01, GE Healthcare) having a bed volume of 5 ml and a binding capacity of 30 mg IgG/ml. By means of the downstream connection of a membrane adsorber ("MA 1", Sartobind® Protein A membrane article No. 93PRAP06HB-12-A, capacity 6.5 mg/ml) with variable dimensioning (0.1-2 ml), the influence of the bed height on the loss of product, the sensitivity of detection and the back pressure during loading of the structure is investigated (Table 1). To this end, the loading experiments are carried out with a mixture of IgG (2.5 mg/ml) as target molecule and BSA (1 mg/ml) as contaminant.

TABLE 1

Number of layers, and size of the total area, of the volume and of the dead volume of the individual membrane adsorbers (MA 1)

| Bed height, mm | No. of layers | Flow area, cm$^2$ | Total area, cm$^2$ | Membrane volume, ml | Dead volume, ml |
|---|---|---|---|---|---|
| 0 | 0 | 0 | 0 | 0 | 0 |
| 0.2 | 1 | 5 | 5 | 0.1 | 0.5 |
| 1 | 5 | 5 | 25 | 0.5 | 0.6 |
| 2 | 10 | 5 | 50 | 1.0 | 1.1 |
| 3 | 15 | 5 | 75 | 1.5 | 1.2 |
| 4 | 20 | 5 | 100 | 2.0 | 1.5 |

To this end, each structure is first equilibrated with ml of buffer A, then loaded with 140 ml of IgG (2.5 mg/ml) and BSA (1 mg/ml) in buffer A, washed with 70 ml of buffer A and then eluted with 50 ml of buffer B. In the chromatogram, the early breakthrough of the contaminant (BSA, $UV_{Contaminant}$=135 mAU) followed by the breakthrough of the target molecules (40-60 ml) ($UV_{Total}$=680 mAU) can be seen (cf. FIG. 2). At the same time, the influence of the downstream membrane adsorber can be seen in an increase in the steepness of the breakthrough curves with increasing size of the adsorber and with an increased capacity (later breakthrough) (cf. FIG. 2).

Figure 1:
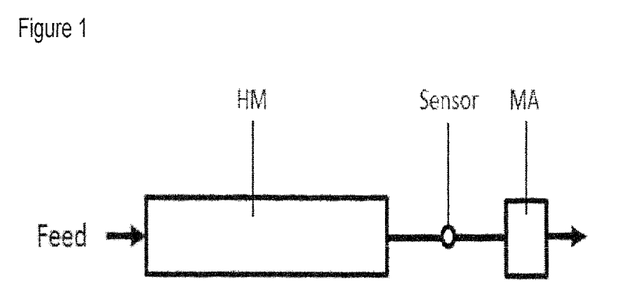
FIG. 1 shows the schematic structure of the present invention comprising main medium (HM; first chromatography system), sensor and second chromatography matrix (MA).
Figure 2:
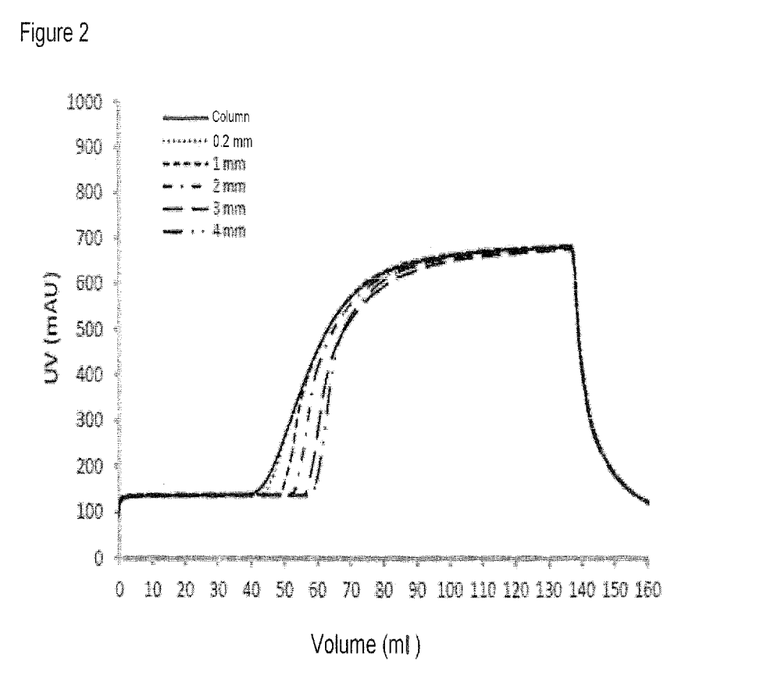
FIG. 2 shows the loading of the HiTrap Protein A unit (first chromatography system) with 140 ml of IgG (2.5 mg/ml) and BSA (1 mg/ml) in buffer A and of a second chromatography matrix with variable bed height (0-4 mm) of Sartobind® Protein A (MA). The breakthrough curves shown correspond to the measurement of the absorption at the output of the column (Column) or after the membrane adsorber (Column+MA 0-4 mm).

In the case of practical application, the additional capacity introduced by the membrane adsorber can be used for the optimal utilization of the column together with a minimization of the loss of product. In the case of the breakthrough curve without downstream membrane adsorber, the termination criterion for loading that is used is the maximum of the first derivative of the UV absorption. In the case of the experiments with downstream membrane adsorber, the maximum of the difference of the signal (in mAU) of the sensor in front of the membrane adsorber within a defined volume interval is used as the termination criterion ($\Delta UV=UV_{X+Y}-UV_X$). The volume interval can be selected on the basis of the concentration of the target molecule in the feed solution, the capacity of the membrane adsorber, and the sensitivity of the sensor used. In this example and the following examples, the volume interval is set conservatively with the dead volume of the downstream membrane adsorber ($\Delta UV=UV_{X+DV}-UV_X$) without taking into account the capacity of the downstream membrane adsorber.

Figure 3:
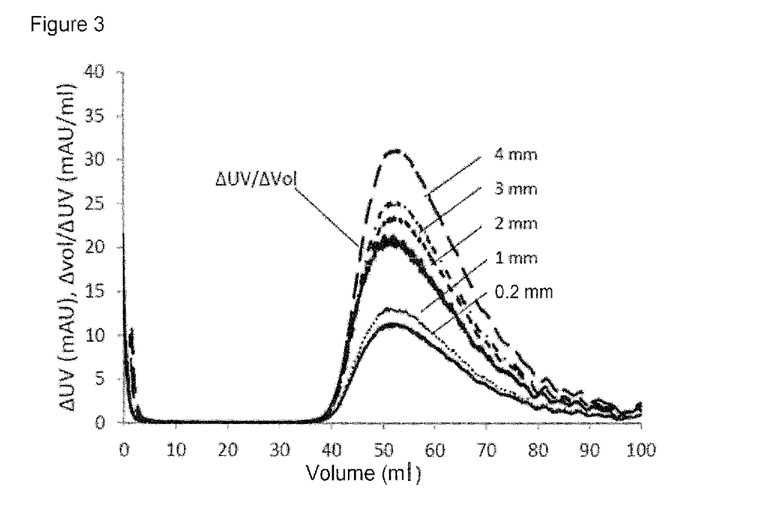
FIG. 3 shows the change in the first derivative ($\Delta UV/\Delta Volume$) or in the $\Delta UV$ signal ($\Delta UV=UV_{x+DV}-UV_x$) with differing bed height of the membrane adsorber, which is connected downstream of the first chromatography system. The signals were determined from the UV absorption values of the sensor, which is situated immediately after the first chromatography system and before the membrane adsorber.

It is possible to identify a distinct relationship from the size of the selected volume difference and the amplitude of the $\Delta UV$ signal, though the position of the maximal values on the x-axis remains the same (cf. FIG. 3). What is noticeable is the larger amplitude of the $\Delta UV$ signal in comparison with the first derivative at larger membrane volumes (1.5 ml and 2 ml), and this is an advantage when determining the breakthrough in the case of poorly detectable signals (in the case of high concentration of contaminants and low concentration of target molecules). Using the described termination criteria, it becomes clear that the enlargement of the volume of the downstream membrane adsorber makes it possible to achieve a minimization of the loss of product from 3% to 0% (cf. Tab. 2).

TABLE 2

$\Delta UV$ signal, pressure during loading, breakthrough of the target substance (IgG) in %, and corresponding loss of product

| Bed height, mm | $\Delta UV$ (mAU) or (mAU/ml) | Average pressure during loading, MPa | Breakthrough, % | Loss of product, % |
| --- | --- | --- | --- | --- |
| 0 | 20.7 | 0.09 | 32.4 | 2.95 |
| 0.2 | 11.3 | 0.09 | 29.9 | 2.14 |
| 1 | 13.2 | 0.10 | 14.8 | 0.63 |
| 2 | 23.4 | 0.12 | 0.6 | 0.20 |
| 3 | 25.1 | 0.15 | 0 | 0.00 |
| 4 | 31.1 | 0.17 | 0 | 0.00 |

Figure 4:
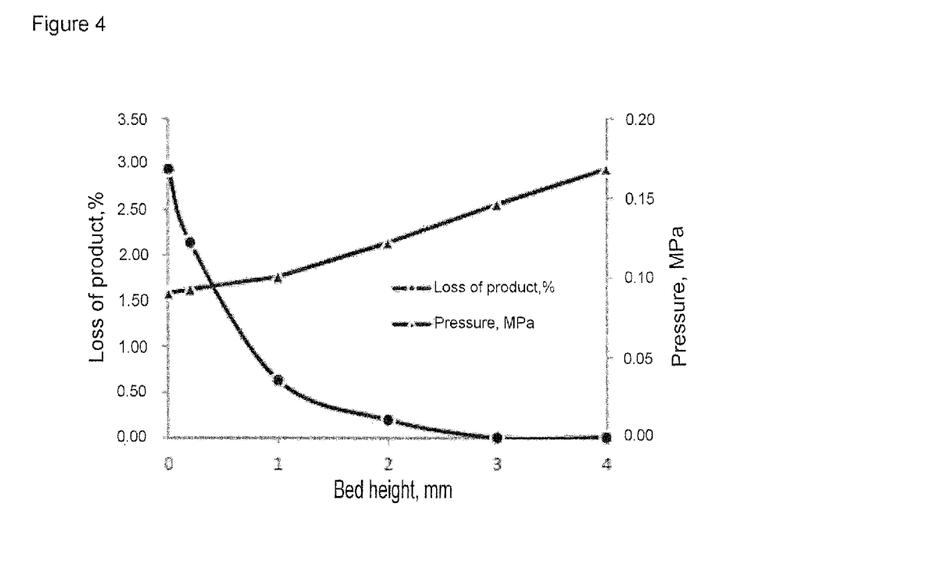
FIG. 4 shows the relationship of the loss of product and of the increase in back pressure depending on the bed height of the downstream membrane adsorber.

At the same time, it is, however, also possible to observe an increase in the back pressure, which correlates with the size of the downstream membrane adsorber (cf. Tab. 2 and FIG. 4). Therefore, the increasing size of the membrane adsorber yields a contrast between of product (which approaches zero) and the increase in the back pressure during loading. This relationship may be crucial for the dimensioning of the membrane adsorber, since it is ideally integrable into already existing systems having a maximum permissible back pressure.

It was possible to load the 5 ml protein A column used here with 152 mg of IgG until complete breakthrough of the target molecule. However, this capacity is generally not fully utilized. To prevent a loss of the target molecule, column materials on a process scale are only loaded to approx. 60% of their capacity (in the case of the column used here, this would correspond to 91 mg of IgG). In the structure described here, a loading of the column with 127 mg of IgG can be realized until the termination criterion is reached, corresponding to an 83% utilization of the existing binding capacity of the column.

Overall, it can be stated that the downstream membrane adsorber can catch target molecules which, during a reliable detection of the breakthrough, were lost after the column. In this connection, the structure benefits from the property of the steeper breakthrough curve following the membrane adsorber, since it is possible as a result to completely avoid loss, even with relatively small dimensioning of the membrane adsorber (6.5% of the capacity of the main medium, 3 mm bed height).

Reference Example 2-Size of the Flow Area of the Downstream Membrane Adsorber

An important parameter in chromatography is the elution of the target molecules. Here, care has to be taken that the elution volume should not be excessively increased by the fitting of an additional membrane adsorber. Furthermore, peak symmetry during elution is an important parameter. The geometry of the membrane adsorber has a crucial influence on the linear flow rate of the sample through the membrane and can thus have an influence on the binding and the elution of the target molecules. To investigate this effect, a solution of IgG (5 mg/ml) and BSA (1 mg/ml) is loaded onto a protein A column and then eluted (cf. FIG. 5) in this experiment. The column (5 ml) is used on its own in one case; it is used with a downstream membrane adsorber having a 5 cm$^2$ flow area in the other case ("MA1") and with a downstream membrane adsorber having a 20 cm$^2$ flow area in the further case ("MA2"), with the same bed volume of 2 ml in both cases, in order to thus achieve a variation of the flow area by a factor of 4 (cf. Tab. 3).

TABLE 3

Properties of the membrane adsorbers used

| | MA 1 | MA 2 |
| --- | --- | --- |
| Flow | Axial | Axial |
| No. of layers | 20 | 5 |
| Bed height | 4 mm | 1 mm |
| Bed volume | 2 ml | 2 ml |
| Flow area | 5 cm$^2$ | 20 cm$^2$ |
| Diameter | 30 mm | 57 mm |
| Membrane area | 100 cm$^2$ | 100 cm$^2$ |
| Dead volume | 1.5 ml | 2.8 ml |

Figure 5:
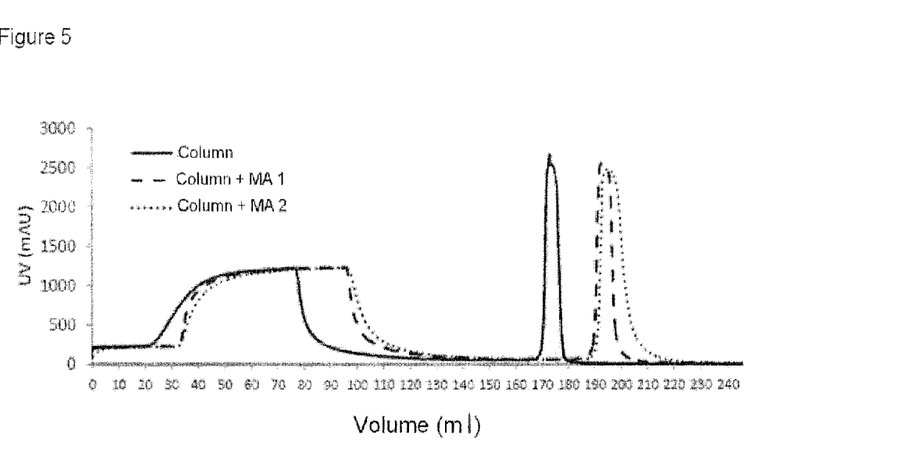
FIG. 5 shows the loading and elution of the HiTrap Protein A column (first chromatography system) having downstream membrane adsorbers (second chromatography matrix) having a 5 cm$^2$ (MA1) and 20 cm$^2$ (MA2) flow area. What is shown are the chromatograms which were detected after the column or after the membrane adsorber (Column+MA1 or MA2) with the aid of a sensor.

To test the effects of the altered flow area, the units were now equilibrated with 50 ml of buffer A (see "Materials and methods"), then loaded with 80 ml (column only) or 100 ml (column+membrane adsorber) of IgG (5 mg/ml) and BSA (1 mg/ml) in buffer A, washed with 70 ml of buffer A, and then eluted with 60 ml of buffer B (cf. FIG. 5).

Besides the already described steeper rise of the breakthrough curve of the target molecule in the presence of the membrane adsorbers (cf. FIG. 5, and also example 1), it is also possible to observe a change in the shape of the elution peak. Especially the tailing factor (T) of the elution peak is an important parameter for describing this circumstance and can be represented by means of a simple equation:

$$T = \frac{a+b}{2a}.$$

Here, a and b are the distances which describe the extent of the elution peak (fronting and tailing) from the peak center at $\frac{1}{10}$ of the maximum peak height (h) (FIG. 5). In the case of a value of T≠1, the peak is asymmetrical, with a value of T<1 describing fronting and a value of T>1 describing tailing. In all cases, it is possible to observe a tailing of the elution peak, it being possible to observe the least tailing in the case without membrane adsorber, only a slight increase in tailing in the case of MA 1 and a distinct tailing in the case of MA 2 (cf. FIG. 5 and Tab. 4).

Furthermore, the elution volume required in order to elute the target molecule from the column was measured (cf. Tab. 4). In general, the results show a rise in the elution volume in the presence of a membrane adsorber, the membrane adsorber having the larger flow area (MA 2) exhibiting a distinct peak broadening and thus a more distinct increase in the elution volume (factor of 2.2) in comparison with the membrane adsorber having the smaller flow area (MA 1, factor of 1.2).

TABLE 4

Influence of the different flow areas on the elution of target molecules

|  | Column | Column + MA 1 | Column + MA 2 |
|---|---|---|---|
| Tailing factor (T) | 1.31 | 1.39 | 1.90 |
| Elution volume (ml) | 7.6 | 9.5 | 16.8 |
| Volume increase | 1.0 | 1.2 | 2.2 |

It has to be assumed that both the dead volume of the membrane adsorber and the linear flow rate along the radial axis have an influence on the binding of the target molecules on the membrane. Therefore, the increase in the elution volume in the case of the unit having a broad flow area can be explained by differences in the residence times in the radial direction of flow. This may be crucial for applications in which a minimization of the elution volume is important (this is generally the case for many applications, since they often involve saving costs for buffers and further dilutions, for example for adjusting the buffer before introduction into a further process step) and must be absolutely observed in the application of the method.

Example 3-Applicability of the Method to Ion-Exchange Chromatography

The general applicability of the method to other chromatographic matrices is demonstrated in the following example by separating a mixture of lysozyme (5 mg/ml) and bovine serum albumin (BSA, 2 mg/ml) by means of anion-exchange chromatography at a pH of 7.4. Whereas lysozyme has an isoelectric point of 11.4, BSA has an isoelectric point of 4.7. Therefore, lysozyme has a positive net charge at the pH used and only binds to a very slight extent to the anion exchanger, whereas BSA is negatively charged and therefore has a strong affinity for the positively charged quaternary ammonium groups R—$CH_2$—$CH_2$—$N^+$ $(CH_3)_3$ of the anion exchanger. Therefore, lysozyme serves as a model for a contaminant and BSA serves as a model for the target molecule. The ligands and the membrane are identical both in the case of the main medium (Sartobind® Q 3 ml membrane adsorber) and in the case of the smaller dimensioned membrane adsorber (MA 1, Sartobind® Q 0.4 ml); both have a dynamic binding capacity of 30 mg BSA/ml (see Tab. 5). However, the two media differ in the dimensioning; the second membrane adsorber is smaller and only has 13% of the capacity of the main medium.

TABLE 5

Parameters of the structure for separating BSA and lysozyme on anion-exchanger membranes (MV = membrane volume)

| Parameter | Main medium | MA 1 |
|---|---|---|
| Flow | Radial | Axial |
| Binding capacity (BSA) | 30 mg/ml MV | 30 mg/ml MV |
| Bed volume | 3 ml | 0.4 ml |
| Dead volume | 4.3 ml | 0.9 ml |

The detection of the loading status takes place at the output of the main medium. To this end, the slope of the UV signal due to the ΔUV value is determined as already described. In this example, the volume interval again corresponds to the dead volume of the downstream membrane adsorber (MA 1, 0.9 ml, cf. example 1). The termination criterion for loading that is selected is the maximal value of the ΔUV curve (approx. 36 ml, cf. FIG. 6).

In this method, a 2% loss of product is achieved in the absence of downstream membrane adsorber (cf. Tab. 6).

TABLE 6

Detection of the breakthrough of BSA

|  | Loading volume, ml | mAU (280 nm) | Breakthrough, % | Loss of product, % |
|---|---|---|---|---|
| Main medium | 36 | 2024 | 29 | 2 |
| Main medium + MA 1 | 36 | 1997 | 0 | 0 |

Figure 6:
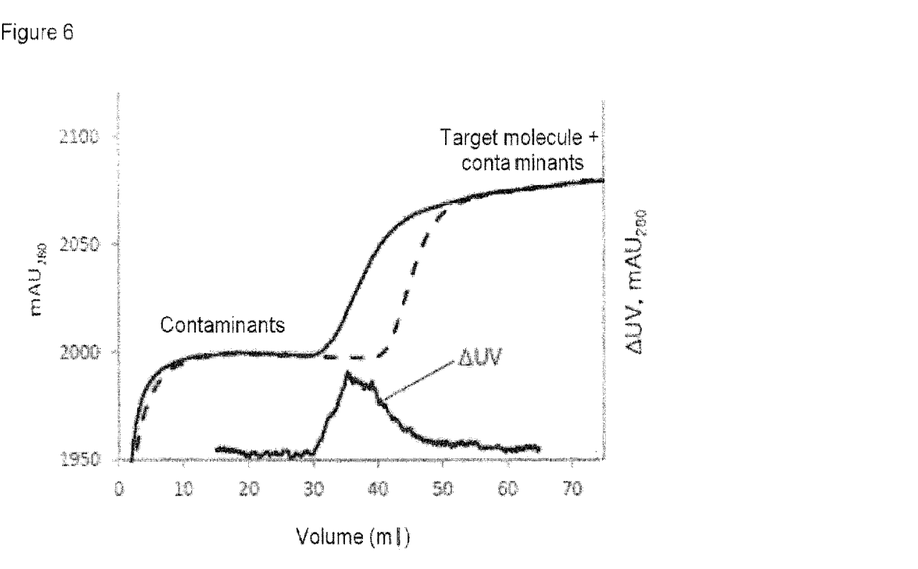
FIG. 6 shows the UV absorption (280 nm) during the loading of the structure described in table 5 with lysozyme (5 mg/ml) and bovine serum albumin (BSA, 2 mg/ml). Owing to the additional membrane adsorber, the breakthrough of the target molecule occurs only at higher loading volume (dashed line, detection after the membrane adsorber). The lower line corresponds to the $\Delta UV$ signal, which was measured before the membrane adsorber.

However, the downstream membrane adsorber catches the majority of the target molecules which did not bind to the main medium (FIG. 6, dashed line). Thus, the loss of product can be minimized (not detectable) when using the membrane adsorber in the case of loading of the main medium until breakthrough of the target molecule and thus optimal utilization of the capacity. The concept is thus absolutely not restricted to protein A chromatography and is readily transferrable to other systems.

The invention claimed is:

1. A device for separating and/or isolating substances in or from a mixture in a fluid, consisting of a first chromatography system which comprises one or more chromatography matrices, a single sensor downstream of the first chromatography system for detecting the substances present in the fluid, and a second chromatography matrix downstream of the single sensor, the second chromatography matrix being connected downstream of the first chromatography system such that the fluid leaving the first chromatography system is guidable through the second chromatography matrix wherein the single sensor for detecting the substances present in the fluid is interposed between the first chromatography system and the second chromatography matrix and determines on a basis of a change in a slope of a breakthrough signal an overloading of the first chromatography system, and wherein said single sensor for detecting the substances present in the fluid is the only sensor comprised in the device, and wherein the combination of the first chromatography system, the second chromatography matrix and the single sensor is present in a unified body.

2. The device as claimed in claim 1, wherein the second chromatography matrix is a convective chromatography matrix such as a membrane adsorber or a monolith.

3. The device as claimed in claim 1, wherein a measurement principle of the sensor is based on UV or IR absorption spectroscopy, terahertz spectroscopy, manometry, conductometry, potentiometry, refractometry, radiometry, fluorescence spectroscopy especially of surface fluorescence quenching, ATR (attenuated total reflection) infrared spectroscopy especially of surface plasmon resonance spectroscopy (SPRS), potentiometry, polarimetry, impendance spectroscopy, NMR spectroscopy, Raman spectroscopy, turbidimetry, nephelometry and on ultrasound transit time, or comprises a combination of multiple techniques as detection principle for the sensor.

4. The device as claimed in claim 1, wherein the first chromatography system has a ligand and the second chromatography matrix has a ligand, the ligand of the first chromatography system and the ligand of the second chromatography matrix each interacting with at least one substance in the mixture via an identical chemical and/or physical interaction, selected from ion exchangers, salt-tolerant ligands, chelating agents, thiophilic or hydrophobic ligands of various chain lengths and configurations, "reversed-phase" ligands, reactive dyes and other dyes, of the inorganic molecules and ions, organic and inorganic compounds thereof, affinity ligands, high-molecular-weight ligands, enzymes and subunits and also parts thereof, structural proteins, receptors and effectors and also parts thereof, viruses and parts thereof, xenobiotics, pharmaceuticals and active pharmaceutical ingredients, alkaloids, antibiotics, biomimetics and of the catalysts.

5. The device as claimed in claim 1, wherein the first chromatography system and the second chromatography matrix have at least one identical ligand which interacts with at least one substance in the mixture via at least one chemical and/or physical interaction, selected from ion exchangers, salt tolerant ligands, chelating agents, thiophilic or hydrophobic ligands of various chain lengths and configurations, "reversed-phase" ligands, reactive dyes and other dyes, of the inorganic molecules and ions, organic and inorganic compounds thereof, affinity ligands, high-molecular-weight ligands, enzymes and subunits and also parts thereof, structural proteins, receptors and effectors and also parts thereof, viruses and parts thereof, xenobiotics, pharmaceuticals and active pharmaceutical ingredients, alkaloids, antibodies, biometrics and of the cataylysts.

6. The device as claimed in claim 1, wherein the first chromatography system and the second chromatography matrix each have at least one different ligand which interacts with at least one substance in the mixture via at least one chemical and/or physical interaction, selected from ion exchangers, salt-tolerant ligands, chelating agents, thiophilic or hydrophobic ligands of various chain lengths and configurations, "reversed-phase" ligands, reactive dyes and other dyes, of the inorganic molecules and ions, organic and inorganic compounds thereof, affinity ligands, high-molecular-weight ligands, enzymes and subunits and also parts thereof, structural proteins, receptors and effectors and also parts thereof, viruses and parts thereof, xenobiotics, pharmaceuticals and active pharmaceutical ingredients, alkaloids, antibiotics, biomimetics and of the catalysts.

7. The device as claimed in claim 1, wherein the fluid leaving the first chromatography system is completely guidable through the second chromatography matrix.

8. The device as claimed in claim 1, wherein a capacity of the second chromatography matrix is smaller than or identical to a capacity of the first chromatography system.

9. The device as claimed in claim 1, wherein the sensor is nondestructive with regard to the target molecule.

10. The device as claimed in claim 1, wherein the sensor is a UV, IR, pH, pressure or conductivity sensor.

11. A method for separating and/or isolating substances in or from a mixture in a fluid, comprising the steps of guiding the fluid through the device as claimed in claim 1 and collecting the fluid which has been guided through.

12. The method as claimed in claim 11, wherein the mixture is a solution of a synthetically or biologically produced product, or a natural substance.

13. The method as claimed in claim 11, wherein the mixture is a protein-containing solution.

14. The method as claimed in claim 11, wherein the mixture is an antibody-containing solution.

15. The use of the device as claimed in claim 1 for separating and/or isolating a target substance in or from a mixture in a fluid.

16. The use of the device as claimed in claim 1, wherein the use of the device allows an improvement in the utilization of the capacity of the first chromatography system.

17. The use of the device as claimed in claim 1, wherein the use of the device allows an over 60% utilization of the capacity of the first chromatography system.

* * * * *